United States Patent
Camus et al.

(10) Patent No.: US 12,042,232 B2
(45) Date of Patent: Jul. 23, 2024

(54) LEFT ATRIAL APPENDAGE CLOSURE GUIDANCE IN MEDICAL IMAGING

(71) Applicant: Siemens Medical Solutions USA, Inc., Malvern, PA (US)

(72) Inventors: Estelle Camus, Erlangen (DE); Tommaso Mansi, Plainsboro, NJ (US); Ingmar Voigt, Erlangen (DE)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 17/805,904

(22) Filed: Jun. 8, 2022

(65) Prior Publication Data

US 2022/0296306 A1    Sep. 22, 2022

Related U.S. Application Data

(62) Division of application No. 15/719,388, filed on Sep. 28, 2017, now Pat. No. 11,432,875.

(51) Int. Cl.
| | |
|---|---|
| *A61B 34/10* | (2016.01) |
| *A61B 8/00* | (2006.01) |
| *A61B 8/06* | (2006.01) |
| *A61B 8/08* | (2006.01) |
| *A61B 90/00* | (2016.01) |

(52) U.S. Cl.
CPC ............ *A61B 34/10* (2016.02); *A61B 8/0883* (2013.01); *A61B 8/483* (2013.01); *A61B 8/5223* (2013.01); *A61B 8/5261* (2013.01); *A61B 8/5276* (2013.01); *A61B 8/065* (2013.01); *A61B 8/466* (2013.01); *A61B 8/488* (2013.01); *A61B 2034/104* (2016.02); *A61B 2034/105* (2016.02); *A61B 2034/108* (2016.02); *A61B 2090/376* (2016.02); *A61B 2090/378* (2016.02)

(58) Field of Classification Search
CPC ...................................... A61B 34/10
See application file for complete search history.

(56) References Cited

U.S. PATENT DOCUMENTS

| 7,702,597 B2 | 4/2010 | Tu et al. |
| 8,116,547 B2 | 2/2012 | Zheng et al. |

(Continued)

FOREIGN PATENT DOCUMENTS

| CN | 106133797 | 11/2016 |
| CN | 106605257 | 4/2017 |

(Continued)

OTHER PUBLICATIONS

Kaminski et al. (2015) Variability of the Left Atrial Appendage in Human Hearts, PloS One, 10(11), e0141901 (Year: 2015).*

(Continued)

*Primary Examiner* — Patrick Fernandes
*Assistant Examiner* — Aminah Asghar

(57) ABSTRACT

An ultrasound imager provides for LAA closure guidance. Using ultrasound imaging allows for modeling over time (e.g., throughout a heart cycle). An anatomy model of the LAA over time is used to create a biomechanical model personalized to the patient. The personalized models and a model of one or more closure devices are used to select a closure device for the patient appropriate for the entire heart cycle and to guide placement of the selected closure device during an implantation.

12 Claims, 4 Drawing Sheets

(56) References Cited

U.S. PATENT DOCUMENTS

| | | | |
|---|---|---|---|
| 8,812,431 | B2 | 8/2014 | Voigt et al. |
| 9,569,736 | B1 | 2/2017 | Ghesu et al. |
| 9,730,643 | B2 | 8/2017 | Georgescu et al. |
| 10,275,876 | B2 | 4/2019 | Reicher |
| 2004/0225212 | A1 | 11/2004 | Okerlund |
| 2008/0319448 | A1 | 12/2008 | Lavallee |
| 2009/0082660 | A1 | 3/2009 | Rahn |
| 2010/0042105 | A1 | 2/2010 | Park |
| 2011/0153286 | A1* | 6/2011 | Zaeuner ............... G06T 19/00 703/1 |
| 2012/0053466 | A1 | 3/2012 | Bianchi |
| 2012/0232386 | A1* | 9/2012 | Mansi ................ G06T 19/00 600/437 |
| 2014/0219537 | A1 | 8/2014 | Carelsen |
| 2015/0112659 | A1* | 4/2015 | Mortier ............... G06T 17/20 703/11 |
| 2015/0182255 | A1 | 7/2015 | Shivkumar |
| 2015/0223773 | A1 | 8/2015 | John |
| 2015/0235569 | A1 | 8/2015 | Babiker |
| 2016/0038246 | A1* | 2/2016 | Wang ................ A61B 6/5217 600/587 |
| 2016/0199198 | A1 | 7/2016 | Dietz |
| 2016/0270859 | A1 | 9/2016 | Park |
| 2017/0000562 | A1 | 1/2017 | Frank |
| 2017/0103532 | A1 | 4/2017 | Ghesu et al. |
| 2017/0150928 | A1 | 6/2017 | del Alamo de Pedro |
| 2017/0270663 | A1 | 9/2017 | Hoffmann |
| 2017/0323481 | A1 | 11/2017 | Tran |
| 2017/0360510 | A1 | 12/2017 | Bischoff |
| 2018/0116725 | A1 | 5/2018 | Ashikaga |
| 2018/0365838 | A1 | 12/2018 | Lorenz |

FOREIGN PATENT DOCUMENTS

| | | |
|---|---|---|
| CN | 107145702 | 9/2017 |
| CN | 107205835 A | 9/2017 |

OTHER PUBLICATIONS

Di Biase, Luigi, et al. "Does the left atrial appendage morphology correlate with the risk of stroke in patients with atrial fibrillation?: Results from a Multicenter study." Journal of the American College of Cardiology 60.6 (2012): 531-538.

Ghesu, Florin C., et al. "An Artificial agent for anatomical landmark detection in medical images." International Conference on Medical Image Computing and Computer-Assisted Intervention. Springer International Publishing, 2016.

Ghesu, Florin C., et al. "Marginal space deep learning: efficient architecture for volumetric image parsing." IEEE transactions on medical imaging 35.5 (2016): 1217-1228.

Grbc, Sasa, et al. "Image-based computational models for TAVI planning: from CT images to implant deployment." International Conference on Medical Image Computing and Computer-Assisted Intervention. Springer, Berlin, Heidelberg, 2013.

Heimann, Tobias, et al. "Real-time ultrasound transducer localization in fluoroscopy images by transfer learning from synthetic training data." Medical image analysis 18.8 (2014): 1320-1328.

Ionasec, et al. "Patient=specific modeling and quantification of the aortic and mitral valves from 4-D cardiac CT and TEE." IEEE transactions on medical imaging 29.9 (2010): 1631-1651.

Mansi, et al. "Quantifying Heart Valves: From Diagnostic to Personalized Valve Repair." Article, p. 1-16.

Mansi, et al. "An integrated framework for finite element modeling of mitral valve biomechanics from medical images: application to MitralClip intervention Planning." Medical image analysis 16.7 (2012): 1330-1346.

Maio, et al. "A CNN Regression approach for real-time 2D/3D registration." IEEE transactions on medical imaging 35.5 (2016); 1352-1363.

Mihalef, et al. "Patient-specific modelling of whole heart anatomy, dynamics and haemodynamics from four-dimensional cardiac CT images." Interface Focus 1.3 (2011): 286-296.

Rajwani, et al. "Left atrial appendage eccentricity and irregularity are associated with residual leaks after percutaneous closure." JACC: Clinical Electrophysiology 1.6 (2015): 478:485.

Zheng, et al. "Multi-part modeling and segmentation of left atrium in C-arm CT for image-guided ablation of atrial fibrillation." IEEE transactions on medical imaging 33.2 (2014): 318:331.

* cited by examiner

LEFT ATRIAL APPENDAGE CLOSURE GUIDANCE IN MEDICAL IMAGING

RELATED APPLICATION

This application is a divisional of U.S. application Ser. No. 15/719,388, filed Sep. 28, 2017, which is hereby incorporated by reference in its entirety.

BACKGROUND

The present embodiments relate to left atrial appendage (LAA) closure. The LAA is an anatomical structure that may facilitate the formation of a life-threatening thrombus. Surgical removal of the LAA structure may treat or prevent the condition. Closure devices may be implanted via a catheter in a much less invasive manner for the patient. These closure devices act like a plug that covers the LAA and prevents the accumulation of blood and formation of thrombus. A key aspect of the procedure is the device selection and planning of the landing zone of the device based on anatomical considerations. Computed tomography (CT) data or three-dimensional transesophageal echocardiography (3D TEE) data may be used to select an appropriate closure device.

In clinical practice, LAA closure planning and guidance uses manual interactions of the physician with ultrasound and CT datasets. Accurate quantification and characterization of the LAA from medical images have been possible so far on CT or DynaCT images. This limited availability is mostly due to the challenging and largely varying shape of the LAA across patients. Machine learning may combine shape modeling and image processing to provide an automatic segmentation with high accuracy from CT and DynaCT data. Once an anatomical model is available, measurements may be automatically derived. However, this approach may not account for variation due to the heart cycle.

Most LAA procedures are performed under three-dimensional TEE or volume intra-cardiac echocardiography (volume ICE) imaging guidance. ICE imaging is performed by the interventional cardiologist, giving the same person control over both x-ray (e.g., fluoroscopy) and ultrasound imaging as well as catheter deployment. Particularly in the case of ICE imaging, 3D Ultrasound imaging is navigated with table-side controls, limiting the complexity of input. Hence, manual measurements may become particularly cumbersome and impact reproducibility.

SUMMARY

By way of introduction, the preferred embodiments described below include methods, computer readable media, and systems for LAA closure guidance with an ultrasound imager. Using ultrasound imaging allows for modeling over time (e.g., throughout a heart cycle). An anatomy model of the LAA over time is used to create a biomechanical model personalized to the patient. The personalized models and a model of one or more closure devices are used to select a closure device for the patient appropriate for the entire heart cycle and to guide placement of the selected closure device during an implantation.

In a first aspect, a method is provided for left atrial appendage closure guidance with an ultrasound imager. A three-dimensional anatomical model of the left atrial appendage of a patient is generated from ultrasound data representing a heart volume of the patient. An image of an ostium of the left atrial appendage is displayed from the ultrasound data. The location of the ostium is determined by the anatomical model. Placement of closure devices with respect to the anatomical model is modeled. The interactions of the closure devices with the anatomical model are simulated with a biomechanical model derived from the anatomical model. Three-dimensional blood flows are computed from the simulated interactions. A first closure device of the closure devices is selected as a function of the blood flow. An image overlaid with a representation of the first closure device at the modeled placement is output.

In a second aspect, a method is provided for left atrial appendage closure guidance with an ultrasound imager. Ultrasound is used to three-dimensional scan a left atrial appendage of a patient over at least a heart cycle. A geometry of the left atrial appendage over the heart cycle is characterized from ultrasound data acquired in the scanning. Placement of a closure device with the geometry of the left atrial appendage is modeled over the heart cycle using a biomechanical model derived from the geometry. Blood flow is computed over the heart cycle based on the modeling. A guidance image shows the placement as optimized based on the modeling and blood flow.

In a third aspect, a system is provided for left atrial appendage guidance. An ultrasound scanner is configured to acquire ultrasound data representing a three-dimensional region of a patient over time. A fluoroscopy scanner is configured to acquire x-ray data representing the three-dimensional region including a transducer of the ultrasound scanner. An image processor is configured to (1) model the left atrial appendage over time based on the ultrasound data, to (2) register coordinates of the ultrasound scanner with coordinates of the fluoroscopy scanner based on the transducer location and orientation as represented in the x-ray data, and to (3) generate an image showing placement of a closure device overlaid on the x-ray-data for the left atrial appendage based on the model and the registered coordinates.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Figure 1:
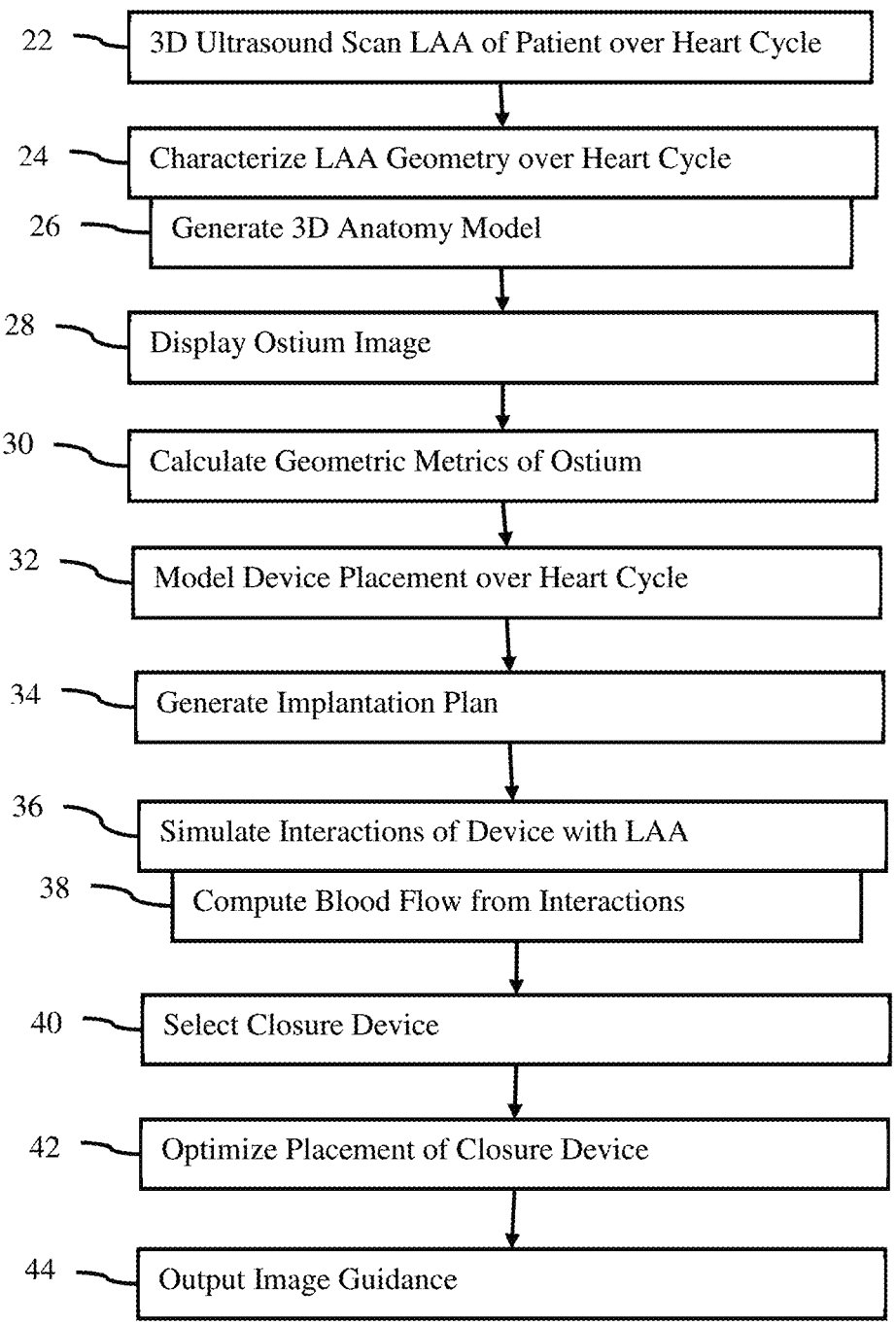
FIG. 1 is a flow chart diagram of one embodiment of a method for LAA closure guidance with an ultrasound imager.

LAA closure guidance is provided with an ultrasound-based system. Ultrasound scanning provides effective LAA closure planning and guidance, from anatomy quantification, device selection, path planning and treatment delivery, with fast, reproducible measurements and quantification tools. The ultrasound-based system enables efficient and robust characterization and quantification of the LAA anatomy. The ultrasound-based system automatically provides intuitive renderings of the LAA for planning and guidance, key measurements, and a simulation system for device selection. An integrated, multi-modality system may combine ultrasound and fluoroscopy imaging.

The anatomical model enables therapy planning through virtual device placement and deployment. Computational models of tissue biomechanics coupled with organ/device interaction models have the potential to simulate device deployment and analyze the resulting tissue deformation and stress, thus providing metrics of anchoring stability, side-effects, and guidance.

In one embodiment, a comprehensive LAA guidance system uses ultrasound scanning for closure device selection and guidance. Three-dimensional (3D) datasets of the LAA are acquired with 3D TEE or volume ICE. The LAA is detected and segmented from the 3D datasets, yielding a 3D model. 3D+time may be handled without loss of generality. Anatomy specific renderings of the acquired datasets are derived and displayed. The derivation and display may be done offline (review mode) or in real-time during image acquisition. Key anatomical measurements and their variation over time are computed from the 3D model. A deployed device is virtually placed and visualized based on the 3D model. Optimal devices may be suggested based on the anatomy (shape, dimensions) and/or a database of clinical reports (e.g. organ shape, success rates). Device position may be dynamically updated throughout the frames of the image sequence by considering the motion of the LAA wall (e.g. through barycentric mapping or machine learning-based motion models). The LAA and/or device metrics and implantation roadmap or pathway, including the optimal trans-septal puncture location, may be automatically calculated. Device deployment is simulated using biomechanical modeling of the device and soft tissue to model the organ-device interactions and predict therapy outcome. For simulation, the mechanical parameters of the anatomical model (e.g. using LA/LAA motion, atrial pressure from Doppler measurements etc.) are personalized. The 3D blood flow before and after virtual device deployment is computed to assess risk of thrombosis and para-device leakages. For multi-modality fusion, anatomy, virtually placed devices, implantation path, and/or roadmap (e.g., including a distance-to-target measurement) may be overlaid on a fluoroscopy image. The device appearance and anatomy may be enhanced in an ultrasound image, such as by using implant location tracked over time in ultrasound and constrained by x-ray implant detection to optimize beam forming and image reconstruction and reduce noise and artifacts.

FIG. 1 shows a method for LAA closure guidance with an ultrasound imager. Ultrasound data representing the LAA over time is used to assist in closure device selection and guidance for placement of a selected closure device. The assistance is personalized to the LAA of a specific patient. Rather than automating what is done by a physician, the method improves on imaging for LAA closure by a combination of actions specific to image processor implementation.

The method of FIG. 1 is implemented in the order shown (e.g., top to bottom or numerical) or a different order. For example, act 40 may be performed based on the geometric metrics calculated in act 30, so performed prior to any of acts 32-38. As another example, act 40 is performed at any time before act 32 where the user manually selects the closure device and uses the selection to model. In another example, the implantation plan of act 34 is generated after the simulation of act 36, the selection of act 40, and/or the placement optimization of act 42. The acts may be performed in sequence within minutes or hours of each other. Alternatively, one or more acts are performed in advance of other acts by days or weeks.

Additional, different, or fewer acts may be performed. For example, act 28 is not performed. As another example, one or more acts 38, 40, and/or 42 are not performed. The simulation of act 36 may not be performed, such as where geometry alone is used for selection in act 40 and/or optimization of placement in act 42.

The method is implemented by a medical diagnostic imaging system, a review station, a workstation, a computer, a picture archiving and communication system (PACS) station, a server, a mobile device, on the cloud, combinations thereof, or other device for image processing medical data. For example, the system shown in FIG. 6 implements the method, but other systems may be used. A hardware image processor of any type of system, interacting with memory (e.g., PACS database or cloud storage), user input device, display device, medical imaging systems, and/or other components, may perform the acts. In one embodiment, an ultrasound scanner performs act 22 and an image processor performs the other acts. The image processor may be part of or separate from the ultrasound scanner.

The acts may be performed automatically by the image processor. The user causes the patient to be scanned or obtains scan data for the patient from a previous scan. The user may activate the process. Once activated, the other acts are performed automatically without further user input. User input of locations of the anatomy in any of the scan data may be avoided. Some user input may be provided, such as for altering measurement locations, altering placement, and/or designating landmarks or other locations.

In act 22, an ultrasound scanner scans the LAA of a patient. 3D TEE, volume ICE, or other scanning may be used. The detection is B-mode, Doppler (e.g., flow mode), and/or other modes of ultrasound imaging.

The scan occurs for one phase of the heart cycle. The scanning may be repeated for other phases to acquire a sequence of ultrasound datasets representing all or part of the LAA over part of a heart cycle, one heart cycle, or multiple heart cycles. The ultrasound data may be data from the processing path derived before generating an image or data for a display as an image.

The scanning is three-dimensional, such as with a wobbler array, a two-dimensional array, and/or parallel beam-formation. Each ultrasound dataset represents the LAA in three dimensions. The scan datasets may be in a spherical or polar coordinate format for scanning or may be interpolated to a regular 3D grid.

The volume region scanned includes the LAA. Other portions of the heart or other tissue may or may not be included. The LAA includes tissue, fluid, and/or other anatomy structures.

The ultrasound data representing the LAA over time allows for automatic quantification of the LAA shape for the particular patient. By automatically quantifying the LAA shape from volume ICE images, the closure device to be used may be selected, and guidance for deployment, including placement, may be provided.

In act 24, a geometry of the LAA is characterized over part or all of a heart cycle or more. The ultrasound data is used to characterize the geometry of the LAA. The geometry is characterized by any measure or parameter of the shape and/or size. The geometry may additionally or instead be characterized by an anatomical model representing the LAA of the patient.

In one approach, boundary detection is used. In other approaches, an anatomical model (e.g., template) is fit to the ultrasound dataset. In yet another approach, a machine-learnt classifier detects the LAA. Any segmentation to detect the LAA may be used. The segmentation may provide the anatomy model, and other measures or parameters are calculated from the segmentation as characterization of the anatomy.

The detection is repeated for different phases or datasets. Alternatively, the fit anatomy model (e.g., mesh representing a detected or segmented surface) from one phase is then tracked through other phases. The geometry is tracked using correlation, speckle tracking, minimum sum of absolute differences or other measures fitting the anatomy model from one phase to the ultrasound data of another phase. In an alternative embodiment, the detection is performed for one phase without a sequence of datasets.

Act 26 represents an example embodiment for characterizing the LAA geometry. A 3D anatomy model of the LAA of the patient is generated from the ultrasound data representing the heart volume. The geometry is a mesh, surface, or other representation of the size and shape of the LAA for the patient.

In one embodiment, the anatomical model is formed based on identified landmarks. The image processor automatically identifies one or more anatomical landmarks (3D points), from which measurements are derived. These landmarks may be a center of LAA orifice, four landmarks at the LAA orifice boundaries, tip(s) of the LAA, LAA lobes, bifurcation(s), and/or any other landmarks of the LAA. Landmarks at neighboring structures (e.g. cross-section of the circumflex artery to indicate level of LAA ostium measurement) may alternatively or additionally be detected.

The landmarks are detected using template matching, machine-learnt classification, or another object detection. Any now known or later developed landmark detection may be used.

For more accurate detection in noisy data, marginal space learning may be applied. A bounding box for the LAA is located in the dataset, and the landmarks are then detected within the bounding box to limit false positives. The bounding box location and detection use a machine-learning approach. Any machine learning may be used, such as a probabilistic boosting tree. In one example, for the bounding box, LAA position, orientation and scale are sequentially estimated using marginal space learning or marginal space deep-learning (MSDL). The algorithm learns from a large annotated database the position, orientation, and scale parameters in an iterative way by subsequently sampling parameter spaces of increasing dimensionality. Using deep learning technologies to learn features or filter kernels that distinguish the position, orientation, and/or scale may increase robustness and accuracy of the approach. At the end of the process, an oriented bounding box around the LAA is provided.

The landmarks are detected within the bounding box. For example, a deep learning approach creates a machine-learnt classifier using learned features from ultrasound data to detect one or more landmarks. One or more such classifiers are applied to detect the landmarks of interest. In another example, a deep image-to-image-network is used to detect a landmark. In yet another example, deep reinforcement learning trains a classifier, which is applied to search through or follow learned acts to find the landmark. The input is restricted to the bounding box or a region around the box.

The output is one or more landmarks. Where machine-learnt detection is applied, various possible locations for a landmark may be identified. A heat map or distribution of probabilities is output. The 3D point with the greatest probability or a 3D point based on a distribution of adjacent higher probabilities may be selected as the landmark. In a semi-automatic approach, the heat map may be displayed with or without an image of the region in the bounding box for user selection of the landmark.

Once the one or more landmarks are located, the 3D anatomical model is estimated from, at least in part, the landmarks. Fit with the ultrasound data may alternatively or additionally be used. The 3D segmentation leverages the landmarks. For example, the anatomical model is a template (e.g., annotated mesh), so the landmark locations in the anatomical model are aligned or registered with the landmark locations as detected for the patient. The landmarks are linked or aligned over time. The rest of the anatomical model may, in one realization, be interpolated or distorted based on the landmark locations and/or fit to the ultrasound data. In another realization, each point of the 3D mesh is fit to the data with a statistical shape model constraining the fit to provide a smooth, natural shape. The anatomical model is a statistical shape model based on landmark distribution across a plurality of patients. The population analytics are used to fit the anatomical model to the detected landmarks for this patient. Algorithms for virtual therapy planning may be used to fit a model of a device or implant. The dynamics of the anatomical model may be used to account for spatial displacement of the device or implant through a heart cycle.

In act 28, the ultrasound scanner and/or image processor, using a display device, displays an image of an ostium of the LAA. The anatomy model includes one or more parts or all of the LAA. Where the anatomy model includes annotation or where the ostium is located as a landmark to fit the anatomy mode, the location of the ostium at one or more phases is known. The ostium location is used to generate an image. For example, the ostium is an oval or other enclosed shape in a plane or generally planar region (e.g., within a slab). A plane or slab (multiple adjacent planes) fit to or most closely aligned with the ostium is determined. A long axis view (see FIGS. 4 and 5) may alternatively or additionally be displayed.

The ultrasound data representing the plane or slab for the ostium is used to generate the image. A planar image (e.g., MPR) is reconstructed from the ultrasound data for the plane. Alternatively, a volumetric slab including the plane with limited depth (e.g., 1 cm) is volume rendered. In yet another embodiment, the volume dataset is clipped based on the plane and the remaining data (e.g., volume beyond the plane–volume extending into the LAA) is volume rendered. The clip-plane rendering is displayed.

Figure 2:
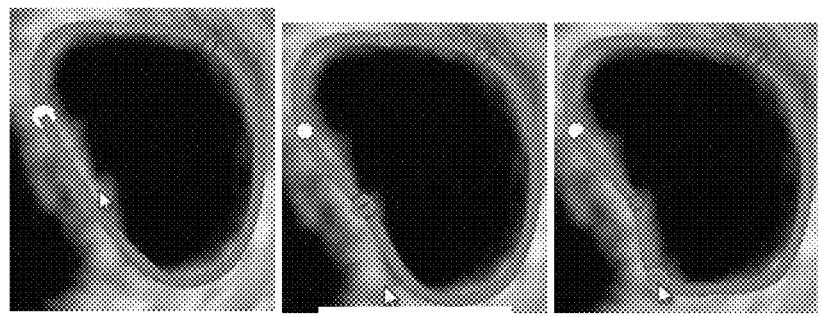
FIG. 2 shows three example images of a displayed ostium of an LAA.

The displayed image may include an annotation for the ostium. FIG. 2 shows three images with the ostium outline as the annotation. The detected locations of the ostium of the LAA are highlighted with a graphic or coloring.

Figure 3:
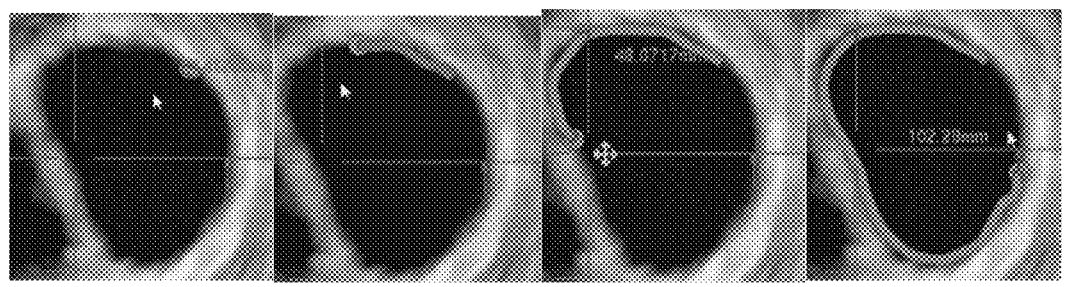
FIG. 3 shows four example images of tracing an ostium of an LAA.

In a semi-automatic or manual approach, the user participates in annotating the displayed image of the ostium or other portion of the LAA. In case of potential segmentation errors, the user may want to refine the automatic segmentation result. Particularly considering table-side operation of the system, convenient user interaction is important. Streamlined editing workflows using smart mesh manipulation and image intensity based editing may be used. For example, a circular cursor or a cursor defined for pressing or pulling on the ostium outline is provided. The user positions the cursor relative to the outline to move the outline (e.g., dilate or shrink the contour and indicate the size of the affected portion by its size). Alternatively, control points are added by the user and the contour or outline is recomputed by fitting a piecewise parametric curve (e.g., splines) to the control points and the ultrasound data. For example, the three images of FIG. 2 represent successive user addition of control points from left to right and the corresponding refit outline. In another embodiment, contour corrections are traced using image based techniques. By searching for higher image intensities closest to the mouse pointer on the image, the user generally traces blood-tissue interfaces to refine the segmentation result. FIG. 3 shows a user manually tracing the ostium from left to right. The image processor then alters the general manual trace to better fit the image based on gradient or intensities over a threshold closest to the outline or mouse pointer. To avoid tracing an image for each phase of the heart cycle, the outline is found in an image for one phase and then tracked through the datasets for other phases. The result of the manual or automatic detection of the ostium is propagated to other phases of the cardiac cycle by tracking.

In act 30, the image processor calculates geometric metrics of the ostium. The metrics may be used to select one or more closure devices for further testing. The metrics may be diagnostically useful for planning intervention by the physician.

Any metric may be calculated. For example, the long axis of the ostium, short axis of the ostium, depth of the LAA, a number of lobes of the LAA, and/or position of lobes with respect to the ostium are calculated from the anatomical model and/or the detected ostium. Other metrics showing the shape of the LAA ostium may be used. The metrics may be at any ostium location, such as the level of the circumflex artery.

Figure 4:
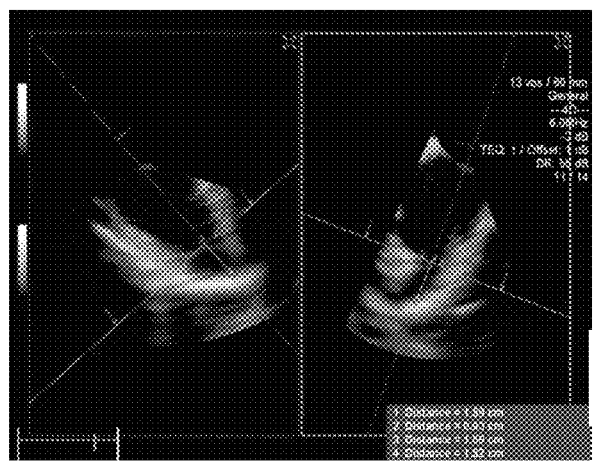
FIG. 4 shows example images for measuring characteristics of the LAA.
Figure 5:
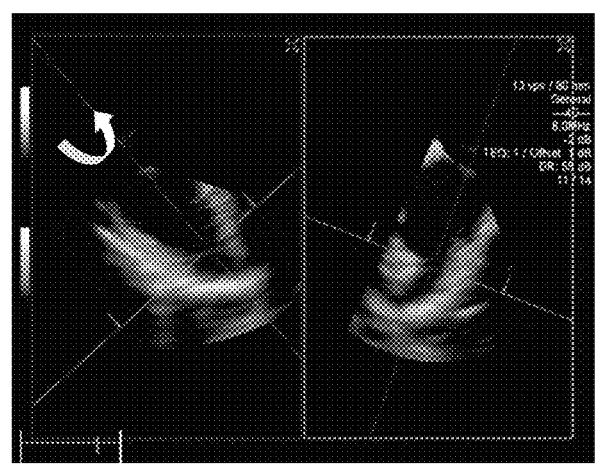
FIG. 5 shows example images for multi-planar reconstructions (MPRs) from a center line of an LAA.

In one embodiment, an oval is fit to the LAA ostium. The long and short axis measurements are derived from the fit oval. An irregularity index may be calculated. The irregularity index indicates how far the actual shape of the ostium is from a perfect oval. Eccentricity, irregularity (e.g., standard or average deviation from oval), and/or other measure of deviation may be used. The area and/or diameter of the ostium contour may be used to measure irregularity or other distortion from a circle, oval, and/or symmetry. Irregularity may correlate with residual leaks for circular LAA closure devices. The depth of the LAA is calculated, such as the maximum distance between the center of the area of the LAA ostium and the deepest structure of the LAA. FIG. 4 shows such a depth measurement on the right side. The left side of FIG. 1 shows measurement of a diameter of the ostium. Based on the automatic quantification, this distance is calculated.

Images from MPRs, volume renderings, and/or of the anatomy model may assist in planning and/or guidance. For example, the ultrasound images of FIG. 4 are displayed, such as showing the line from the center of the LAA ostium to the deepest structure of the LAA. An additional display functionality allows the user to visualize MPR planes that rotate 360° around this line. FIG. 2 shows two ultrasound images for perpendicular planes along center line of the LAA (rotation around center line shown by arrow).

Some LAA structures contain more than one hollow structure. LAA lobes are smaller hollow structures that branch off the main hollow structure of the LAA. To deploy the closure device successfully, the number of lobes is determined. The lobes may be detected and visualized. The closure device is to be positioned such that the closure device covers the ostiums of these lobes. Metrics may be calculated for the lobes. The lobes may be detected from annotations of a fit model, by machine-learnt classification, and/or by template matching. The lobes may be visualized in different colors, making anatomical understanding easier to the user.

Any of the metrics are calculated for a given phase. The same metrics may be calculated for other phases. The resulting values as a function of time may be displayed to the user in a table or as a graph. The depth axis may be displayed in a 3D rendering of the LAA as a moving axis as a function of time.

In act 32, the image processor models placement of one or more closure devices in the LAA. The physician may select a closure device to test. Alternatively, the image processor selects based on the metrics. The shape and/or size of the LAA and/or ostium of the LAA is used to select the closure device. More than one closure device may be selected for testing. The placement of closure devices with respect to the anatomy model is modeled. The geometry of the closure device is modeled with respect to the geometry of the anatomy model.

The placement is modeled for one phase. Alternatively, the placement is modeled in different, such as all, of the phases. The placement is modeled over the heart cycle. Since the anatomy and corresponding anatomy model varies over the heart cycle, the placement is modeled with respect to different phases. The image processor updates the placement through the sequence or over the heart cycle.

The fit of the closure device with the LAA may be measured for any given placement. Any fit measure may be use used, such as a minimum sum of absolute differences or standard deviation. The fit may be measured for different phases and provided as a graph or average. The image processor calculates the fit, such as a geometric fit, of each selected closure device to the anatomical model.

The placement is modeled using geometry. The modeling is based on geometry of the closure device and geometry of the LAA. In alternative or additional embodiments, the placement is modeled using a biomechanical model for the LAA, allowing for simulation of interactions distorting the geometry of the closure device and/or anatomy model. Act 36 deals with this simulation.

In one embodiment of geometric modeling, the geometric fit is used for selection and to plan for device delivery by optimizing placement. The modeling provides a virtual LAA closure. A geometric model of the closure device is positioned relative to the geometric or anatomy model of the LAA. From the anatomical model, a default position is automatically computed, such as orienting a center of the closure device at a center line of the LAA through the center of the ostium. Alternatively or additionally, the user may interactively place or adjust the position of the device. The adjustment is in translation and/or rotation along any axis. The position of the closure device model is then dynamically updated throughout the frames of the image sequence by considering the motion of the LAA wall, and assuming a constant device-to-LAA position relationship (e.g. through barycentric mapping) or, in more advanced settings, by applying learned motion from a database of already implanted patients.

From the device position in one or more phases, the image processor automatically calculates LAA-to-device fit metrics. Example fit metrics include over-sizing or under-sizing (e.g., average difference in size). To find the fit for different closure devices, different closure device geometric models are used. These closure device models may be imported models from device manufacturers or created from 3D scans.

Different positions of the closure device to the LAA may be tested for geometric fit. The position with the optimum or best geometric fit through the phases may be identified. This optimum position of the virtual device may be used during deployment as an image overlay for guidance on the ultrasound image or the fluoroscopy system.

The LAA shape is subject to a considerable spectrum of morphological variation (e.g. "Cactus", "Chicken Wing", "Windsock", "Cauliflower") with potential impact on device selection and position. The image processor, based on optimum placement for each device, may suggest the device to use. Alternatively or additionally, the devices may be suggested based on the anatomy (shape, dimensions) and/or a database of clinical reports using morphologic similarity. Similar patient cases may be ranked using correlation, such as by applying a machine-learnt classifier. The similar cases may be presented to the physician based on the device, similarity of LAA geometry, and outcome. Any outcome information may be used, such as average residual leaks and/or years until follow up intervention.

In act 34, the image processor generates an implantation plan. The implantation plan includes the placement of the closure device relative to the LAA of the patient. Other information may be included in the plan, such as a location of a trans-septal puncture for accessing the LAA. The path along which the catheter proceeds and the puncture location are included in the plan. A set of different plans may be provided and one of them selected based on the position of the ostium relative to other parts (e.g., segmented left and right atrial) of the heart and/or based on the placement position of the closure device relative to the LAA. Alternatively, the path is calculated from geometric information. A roadmap, including the optimal trans-septal puncture, for optimal device deployment is generated to guide deployment.

In act 36, the image processor simulates interactions of one or more of the closure devices with the anatomy model. The interaction provides more than geometric fit or geometric information. The interaction uses a biomechanical model derived from the anatomy model. The biomechanical model uses material properties and physics to model the distortions and/or effects of forces due to interaction between the closure device and the LAA.

The simulation is performed over multiple phases. The LAA is subjected to heart motion forces that vary by phase. This variation is accounted for in the biomechanical model to determine the interaction and corresponding effects over the various phases of the closure device.

To personalize the biomechanical model, the anatomy model, ultrasound measures of tissue or flow (e.g., perfusion and/or elasticity), and/or other information may be incorporated. The biomechanical model may use the finite element method, wavelets, or other representation interrelating various characteristics.

This simulation may be used to refine or may be incorporated into placement determination, generation of the implantation plan, selection of the closure device, diagnostic information, outcome prediction, and/or other uses. While geometric fitting of a deployed device model may provide insights, the simulation with the biomechanical model provides predictions on resulting changes in LAA and/or left atrial anatomy, along with potential changes in blood flow patterns. To provide this information, the biomechanical model is a predictive computational model of anatomy function and LAA-to-device interactions.

In one embodiment, the biomechanical model is personalized to the patient using the ultrasound data from the patient. The pathophysiology for the patient is captured. The biomechanical model represents the LAA with or without left atrial tissue. The biomechanical model is derived from the anatomical model. The atrial wall and the LAA is estimated either directly from the ultrasound data (e.g., from the anatomy model) or by fitting a template (e.g., atlas model) or statistical shape model by varying thickness and extruding. The thin volume surface is then meshed with volumetric elements (e.g. tetrahedron or hexahedron).

The mesh of this anatomy model may be used with a biomechanical solver to calculate the displacement of the atrial wall and LAA given internal and external forces. Internal forces account for tissue elasticity (transverse isotropic and nearly incompressible) and active stress (to capture the active contraction of the atrial muscle). External forces account for the boundary conditions (e.g., tethering to vessels and left ventricle, pericardium bag, etc.) and hemodynamics (left atrial pressure, wall shear stress, etc.). The forces are handled with a Newton equation for soft tissue mechanics.

Further personalization is performed for some or all of the force calculations. For example, the ultrasound data over time provides tissue motion, such as motion of the anatomy model over time. From the observed motion of the left atrium and LAA and given a set of boundary conditions and pressure, the elasticity of the tissue may be estimated globally and regionally, such as solving for elasticity as an inverse problem from the motion or by applying a machine-learnt classifier. Alternatively, the elasticity is measured using ultrasound scanning. If atrial pressure is available (e.g. through echo Doppler or by direct catheter measurement), the estimation of the active and passive stress becomes possible. Alternatively, the pressure is derived from a cuff-measured pressure. Availability of magnetic resonance imaging allows regional modification of tissue parameters to capture variations in tissue substrate, such as level of fibrosis. Elasticity scanning may be used to determine level of fibrosis assuming fibrosis correlation with stiffness. Alternatively, the level of fibrosis is assumed or based on a patient average.

For simulating the interaction, the closure device is modeled. A computational model of the device mechanics and dynamics is used. For the computational mechanics, a finite element method is used to solve for elasticity. More efficient solvers, such as the mass-spring method, may be used. The parameters of the device (e.g., Young modulus, shape memory) may be directly obtained from the specifications (e.g. Young modulus given known material) based on the material composition and dimensions. Alternatively, indirect assessment is performed. For example, dimensions and shape are obtained by scanning a deployed device with a CT imaging scanner. Mechanical parameters are estimated using bench testing by measuring strain given a certain stress and known boundary conditions.

After the biomechanical model of the LAA is fit or personalized based on the mechanical parameters and the anatomy model, the image processor simulates the interactions between the biomechanical model and the device computational model. The LAA-to-device interactions are modeled using contact forces. To ensure coupling, the equations of the models are solved at the same time, such as using an iterative solution. For each time step, contacts are determined and forces are applied to the biomechanical model of the LAA and the computational model of the device at the contact points following the action-reaction principle. The force is modeled as a spring. Other force representations may be used, such as accounting for friction. The solution provides for the forces and resulting shape or geometry distortions of the LAA and the closure device.

In act 38, the image processor computes three-dimensional blood flows from the simulated interactions. The blood flow at a given phase may be calculated based on the geometry as distorted and any boundary conditions (e.g., pressure and flow). In other embodiments, the blood flow is computed using hemodynamic equations. The change in position, size, shape, or other change over time is included in determining the effect on blood flow. The computation solves for the blood flow at different phases, such as all or at least part of the heart cycle.

For hemodynamics, computational fluid dynamics (CFD) is used to estimate blood flow through or by the LAA. The CFD equations are solved based on the Lattice-Boltzmann method (LBM). Other solutions may be used. Given the anatomy, dynamics, and biomechanics, the resulting blood flow in the left atrial and/or LAA is computed. To perform patient-specific simulations, the geometry and the velocity at each node of the model are passed to the flow solver as boundary conditions. In a two-way fluid-structure-interaction setup, the resulting fluid force (wall stress) is passed back to the biomechanical solver previously presented as boundary conditions to the wall and device mechanics. The computation of flow and interaction simulation are performed simultaneously or as part of an iterative solution for both blood flow and interaction. Alternatively, the blood flow computation is based on already simulated interactions.

The flow may be computed before virtual implantation to assess potential low turbulence areas, risk of thrombosis, or other information. The computation does not include the interaction with a closure device. The flow may be computed for after virtual implant by including the model of the closure device. The flow with the closure device may be used to assess risks of para-device leak or other information. Change in flow from before and after placement of the closure device may be calculated.

In act 40, the image processor selects a closure device. Closure devices of the same type or brand but different sizes may be used. Closure devices of different types and/or brands but a same size may be used. Closure devices of different shapes and/or materials may be used. Several devices adapt to different anatomical shapes of the LAA (e.g., Watchman from Boston Scientific, Amplatzer/Amulet from St. Jude Medical). The selection is of one of the closure devices over others.

The geometric fit, para-device leakage, or other information is used to select one closure device over others. The selection may be prior to modeling or simulation or may result from results of the modeling or simulation. The selection may be based on results for testing one device (e.g., comparing values for metrics to thresholds). Alternatively, the selection is based on comparison of modeling or simulation of multiple devices. For example, the blood flow (e.g., leakage) is calculated for each of multiple different closure devices. The closure device (e.g., due to size and/or shape) with the least leakage is selected.

The selection is based on information for a given phase. Since ultrasound scanning provides datasets for different phases, the selection of the closure device may be based on information over the phases. The average or maximum leakage or other blood flow characteristics may be used.

Other criteria than blood flow may be used instead or in addition to blood flow. The type, material, shape, and/or size of the closure device is selected based on elasticity in the biomechanical model, positions of the closure devices with resulting leakages, wall displacements in the anatomy model through a heart cycle, and/or stresses at anchoring positions of the closure devices.

In one embodiment, the elasticity of the wall and resulting deformation due to interaction is used with leakage. The goal is to provide little leakage with minimal deformation given the elasticity for selecting the device and size. The apparent orifice diameter might not be enough to ensure proper anchoring. The modeling may also provide other information, such displacement of the walls and interactions with neighboring structures during a complete heart cycle and/or stress at the anchoring position to assess potential risk of device embolization.

Rather than the image processor making the selection, the information may be provided to the user. The leakage, interactions, and/or other information for different closure devices (e.g., different sizes, shapes, and/or constructions) are presented. Images of the interaction and/or blood flow over time, charges of leakage over time, and/or other information assist the user in selecting a closure device.

In act 42, the image processor optimizes the placement of the closure device. The placement is performed automatically, but semi-automatic placement based on user adjustments may be used.

The optimum placement is determined based on geometry, metrics from the geometry, modeling of geometric fit, and/or simulated interaction. The placement may consider tissue characteristics for anchoring and/or leakage over time. The differences in force resulting from different placements and/or the amount of tissue or device distortion may be used to optimize the placement.

The criterion or criteria are used to optimize the placement. Different placements may be used to minimize leakage, maximize geometric fit, or otherwise optimize placement. With multiple considerations, weighted combination may be used to determine the optimal placement.

In act 44, the image processor outputs an image. The image is used as part of modeling, simulating, characterizing geometry, calculating geometric metrics, or other action. Alternatively or additionally, the image is provided to guide the intervention to implant the device in the patient.

The image is an ultrasound image. Other types of imaging may be used, such as a fluoroscopy image. An image of just a plane (e.g., MPR) or volume renderings of a volume, clipped volume, or thin slab (e.g., 10 planes or fewer) may be generated.

The image is overlaid with a representation of the closure device, such as the selected closure device at the optimized position. The image may be used to guide placement of the actual closure device during the implantation. For example, a fluoroscopy or ultrasound image includes a graphic representing the desired placement of the closure device relative to anatomy. As the image is updated due to scanning, the graphic is maintained relative to the anatomy to indicate the location of deployment. The path and/or puncture site may be represented as well. Other information may be provided, such as a distance of a catheter tip or closure device from a puncture site and/or deployment location.

Multi-modality guidance may be provided. Multi-modality imaging guidance is desired for enhanced workflow and outcomes. In the case of the LAA closure procedure, fluoroscopy is used for guiding the delivery catheter and the device deployment while 3D TEE or volume ICE is used to guide trans-septal puncture and positioning of the device or delivery catheter before deployment of the device in the LAA. Fluoroscopy is a 2D projection that provides good visualization of the delivery catheter and device; however, it does not provide information on the 3D shape and hemodynamics of the LAA. This information may be obtained with 3D TEE or volume ICE.

The 3D anatomy model of the LAA or a live 3D image of the LAA may be registered with fluoroscopy and overlaid on the fluoroscopic 2D projection image. The user may determine and mark the optimum location of the puncture site on the septum for the delivery catheter. This location is overlaid as a graphic or highlighting (e.g., adding color) on the imaging. Then, the trans-septal puncture is performed using fluoroscopy, 3D TEE or volume ICE guidance, or a combination of fluoroscopy and 3DTEE or volume ICE. After the trans-septal puncture is performed, the delivery catheter is advanced into the left atrium pointing towards the LAA. Fluoroscopy with or without ultrasound imaging is used to guide the positioning of the delivery catheter.

In a next step, the closure device is inserted and advanced to the tip of the delivery catheter. The actual closure device is positioned at the optimum position in the LAA by displaying the fluoroscopy image (live or previously acquired) registered with the live 3D TEE or volume ICE image. The registration allows the calculated optimal position to be displayed (e.g., displayed as a marker or rendering of the device) on either or both types of imaging. The virtual placement is shown on one or more images to guide placement of the actual closure device. Once the actual device is close enough to the optimal position, the system shows a corresponding message (e.g. green flag or distance measure). The actual device may then be deployed fully using fluoroscopy or a combination of fluoroscopy and 3D TEE or volume ICE.

After deployment, a tug test is performed to ensure that the closure device is sufficiently and correctly anchored in the tissue. Following a successful tug test, the closure device is released (e.g., detached from the delivery catheter). After release, it is again possible to visualize the position of the actual closure device together with the calculated optimal position in a 3D rendered view (3D TEE or volume ICE).

The coordinate system of the ultrasound scanner or transducer is spatially registered with the coordinate system of the fluoroscopy scanner. A spatial transform resulting from the registration results in locations in one coordinate system being known in the other coordinate system, allowing anatomy and/or device locations in one being transferrable to the other. Any registration may be used. In one embodiment, the position and orientation of the transducer (e.g., TEE probe or ICE catheter) is detected in the fluoroscopy image. Machine-learnt classification, template matching, landmark detection, fiducial location, or other detection may be used. The ultrasound coordinates are based on the transducer, so the position and orientation in the fluoroscopy image of the transducer provides the spatial transform relating the coordinate systems. The echo-fluoro registration provides a transformation matrix that puts both imaging modalities in the same coordinate system.

The placement, implantation path, and anatomy model are found using ultrasound. The placement, implantation path, and anatomy model may be added, overlaid on, or used to highlight or mark locations on the ultrasound and fluoroscopy images. Similarly, the information provided by the fluoroscopy images may be used to enhance the ultrasound images. For example, devices detected in the fluoroscopy images may be tracked over time using fluoroscopy. Such devices include catheters, implanted objects, or other x-ray opaque structures. The detection uses any of the detections discussed above for the catheter. An overlay or other marker of the device detected in fluoroscopy may be added to ultrasound images.

The same object may be detected in both modes of imaging. The position of the object may be refined, such as by averaging the position, using the detection in both modes of imaging.

Co-registration and ultrasound enhancement may be further exploited during ultrasound image formation. For example, the position and orientation of the transducer is detected in fluoroscopy. That position and orientation relative to the LAA may be used to control beamforming (e.g., scan from a direction more normal to the LAA or to avoid shadowing from acoustically opaque tissue or bone), for noise or artifact reduction (e.g., motion correct for transducer motion), and/or for image reconstruction (e.g., more or less temporal filtering depending on amount of movement).

The use of the method for planning LAA closure and/or for guiding LAA closure is described above. The method or parts of the method may be used for closure device design. During development, different shapes, sizes, materials, structures, or other design aspects are changed and tested through geometric fit, placement determination, and/or simulated interactions to validate the design, durability, and/or ease of use.

Figure 6:
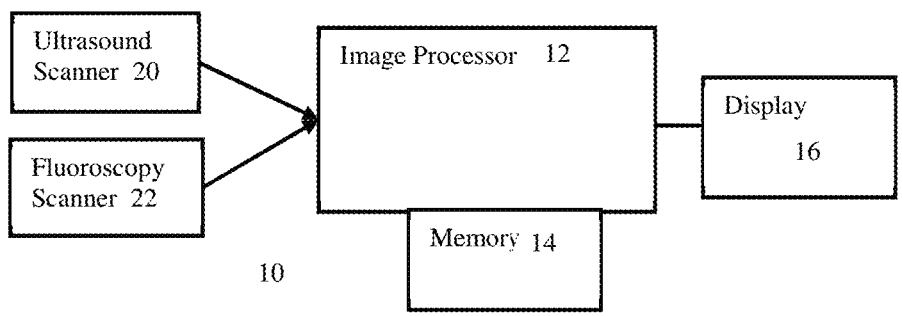
FIG. 6 is a block diagram of one embodiment of a system for LAA closure guidance.

FIG. 6 shows a system 10 for LAA closure guidance. The system implements the method of FIG. 1 or another method. For planning the guidance, the system personalizes models to the patient (e.g., an anatomy model and a biomechanical model) and determines a closure device to use and optimal placement of the closure device. During implantation of the selected closure device, the system guides the placement of the closure device in the patient.

The system includes an image processor 12, a memory 14, a display 16, ultrasound scanner 20, and a fluoroscopy scanner 22. The image processor 12, memory 14, and display 16 are shown separate from the imaging modalities 20, 22, such as being part of a workstation, computer, or server. In alternative embodiments, the image processor 12, memory 14, and/or display 16 are part of one or more of the imaging modalities 20, 22. In yet other embodiments, the system 10 does not include the imaging modalities 20, 22. Additional, different, or fewer components may be used.

The ultrasound scanner 20 is a medical diagnostic ultrasound scanner. The ultrasound scanner 20 includes a transducer (e.g., wobbler or two-dimensional array) and parallel receive beamformer for real-time 3D scanning. The ultrasound scanner 20 includes detectors or other image processors to generate images from acoustic echoes received by the transducer. By repeating scanning, a sequence of ultrasound datasets is provided. The sequence represents different phases through one or more heart cycles.

The fluoroscopy scanner 22 is an x-ray system, such as a C-arm x-ray system, angiography system, or dedicated fluoroscopy system. An x-ray source is mounted opposite a detector with an intervening patient space. X-rays from the source pass through the patient and impinge on the detector, providing projection fluoroscopy images. Fluoroscopy images are acquired at any frequency and represent a 3D region of the patient, including the ultrasound transducer, projected to a plane.

The memory 14 is a buffer, cache, RAM, removable media, hard drive, magnetic, optical, database, or other now known or later developed memory. The memory 14 is a single device or group of two or more devices. The memory 14 is shown associated with or part of the image processor 12, but may be outside or remote from other components of the system 10. For example, the memory 14 is a PACS database storing the scan data from the modalities 20, 22.

The memory 14 stores the scan data, models, values for metrics, and/or information used in image processing, simulating interaction, determining geometric fit, fitting an anatomy model, modeling a closure device, or other acts. The memory 14 is additionally or alternatively a non-transitory computer readable storage medium with processing instructions. The memory 14 stores data representing instructions executable by the programmed image processor 12. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The image processor 12 is a general processor, digital signal processor, three-dimensional data processor, graphics processing unit, application specific integrated circuit, field programmable gate array, digital circuit, analog circuit, quantum computer, combinations thereof, or other now known or later developed device for LAA closure guidance. The image processor 12 is a single device, a plurality of devices, or a network. For more than one device, parallel or sequential division of processing may be used. Different devices making up the image processor 12 may perform different functions, such as an automated anatomy detector and a separate device for modeling geometric fit and simulating interaction. In one embodiment, the image processor 12 is a control processor or other processor of a medical diagnostic imaging system, such as the ultrasound scanner 20 or the fluoroscopy scanner 22. The image processor 12 is a hardware device configured by or operating pursuant to stored instructions, design (e.g., application specific integrated circuit), or hardware to perform various acts described herein.

The image processor 12 is configured to model the LAA over time based on the ultrasound data, register coordinates of the ultrasound scanner with coordinates of the fluoroscopy scanner based on the transducer location and orientation as represented in the x-ray data, and to generate an image showing placement of a closure device for the LAA based on the model and the registered coordinates. The image processor 12 may generate the image for placement based on performing characterization of the LAA geometry, ostium or other geometric metrics, modeling device placement, determining an implantation plan, simulating interactions of the device with the LAA using computation and/or biomechanical modeling, computing blood flow based on hemodynamics, selection of the closure device, and/or optimizing placement.

The display 16 is a CRT, LCD, plasma, projector, printer, or other output device for showing an image or other output of the image processor 12 and/or modalities 20, 22. The display 16 displays an image of the detected anatomy, geometric metrics, simulated interaction, closure device placement, and/or other guidance information.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for left atrial appendage closure guidance with an ultrasound imager, the method comprising:

three-dimensional scanning a left atrial appendage of a patient with ultrasound over at least a heart cycle;

characterizing a geometry of the left atrial appendage over the heart cycle from ultrasound data acquired in the scanning, the characterizing comprising generating a three-dimensional anatomy model of the left atrial appendage of a patient as the geometry, the three-dimensional anatomy model generated from the ultrasound data representing a heart volume of the patient, the three-dimensional anatomy model of the left atrial appendage generated from the ultrasound data from landmark detection including detection of a center of the left atrial appendage, an orifice boundary, tips of the left atrial appendage, left atrial appendage lobes, and bifurcations;

modeling placement of a closure device with the geometry of the left atrial appendage over the heart cycle using a biomechanical model derived from the geometry;

computing blood flow over the heart cycle based on the modeling;

generating a guidance image showing the placement as optimized based on the modeling and blood flow, wherein generating the guidance image comprises outputting the guidance image showing anatomy of the patient including a first image of an ostium of the left atrial appendage, the anatomy overlaid with a representation of the closure device at the modeled placement.

2. The method of claim 1 wherein characterizing comprises fitting an anatomy model at one phase of the heart cycle, the geometry comprising the fit anatomy model at the one phase, and tracking the geometry at other phases of the heart cycle.

3. The method of claim 1 further comprising optimizing the placement based on metrics calculated from the modeling and the geometry.

4. The method of claim 1 further comprising displaying the first image of the ostium of the left atrial appendage from the ultrasound data, determining a location of the ostium from the geometry generated from the ultrasound data, the location of the ostium defining a position of an image plane or slab for the ostium where the first image of the ostium is limited to the image plane or slab.

5. The method of claim 1 wherein three-dimensional scanning comprises transesophageal echocardiography or intra-cardiac echocardiography.

6. The method of claim 1 wherein generating the guidance image comprises displaying with a clip plane or a planar reconstruction for an image plane or slab based on a location of the ostium in the geometry.

7. The method of claim 1 further comprising calculating, by a processor, a long axis of the ostium, short axis of the ostium, depth of the left atrial appendage, and a number of lobes of the left atrial appendage;

further comprising selecting the closure device from a group of different devices, the closure device selected as a function of the blood flow, the long axis of the ostium, the short axis of the ostium, the depth of the left atrial appendage, and the number of lobes of the left atrial appendage.

8. The method of claim 1 wherein modeling the placement comprises selecting the closure device based on a shape and/or size of the geometry, updating the placement through a sequence representing the geometry over a heart cycle, and calculating a geometric fit over the sequence of the closure device to the geometry.

9. The method of claim 1 further comprising generating an implantation geometric plan including a location of trans-septal puncture based on the placement.

10. The method of claim 1 further comprising selecting a type and/or size of the closure device based on measurements of elasticity in the biomechanical model, leakage resulting from the placement, wall displacements in the geometry through a heart cycle, and stresses at anchoring positions of the closure device.

11. The method of claim 1 wherein generating comprises outputting the guidance image as a fluoroscopy image with the closure device at the modeled placement and a distance-to-target value of a current position of a device in the patient with the representation.

12. A system for left atrial appendage guidance, the system comprising:
an ultrasound scanner configured to three-dimensionally scan a left atrial appendage of a patient with ultrasound over at least a heart cycle;
an image processor configured to characterize a geometry of the left atrial appendage over the heart cycle from ultrasound data acquired in the scan and user edits on a first image of an ostium of the left atrial appendage from the ultrasound data, the image processor configured to determine a location of the ostium from the geometry generated from the ultrasound data, the location of the ostium defining a position of an image plane or slab for the ostium where the first image of the ostium is limited to the image plane or slab, the image processor configured to model placement of a closure device with the geometry of the left atrial appendage over the heart cycle using a biomechanical model derived from the geometry, and the image processor configured to compute blood flow over the heart cycle based on the model of the placement of the closure device with the geometry; and
a display configured to display the first image and to display a guidance image overlaid on the first image, the guidance image showing the placement as optimized based on the modeled placement and blood flow.

* * * * *